United States Patent
Kwon et al.

(10) Patent No.: US 8,183,405 B2
(45) Date of Patent: May 22, 2012

(54) OBOVATOL DERIVATIVES OR PHARMACEUTICALLY ACCEPTABLE SALTS THEREOF, PREPARATION METHOD THEREOF AND PHARMACEUTICAL COMPOSITION FOR THE PREVENTION AND TREATMENT OF CANCER CONTAINING THE SAME AS AN ACTIVE INGREDIENT

(75) Inventors: Byoung-Mog Kwon, Daejeon (KR);
Dong Cho Han, Daejeon (KR);
Su-Kyung Lee, Chungcheongbuk-do (KR); Hye-Nan Kim, Daejeon (KR);
Young-Min Han, Daejeon (KR);
Dae-Seop Shin, Chungcheongbuk-do (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 496 days.

(21) Appl. No.: 12/219,726

(22) Filed: Jul. 28, 2008

(65) Prior Publication Data

US 2009/0239955 A1   Sep. 24, 2009

(30) Foreign Application Priority Data

Mar. 24, 2008   (KR) ........................ 10 2008-0026954

(51) Int. Cl.
*C07C 69/66* (2006.01)
*C07C 69/34* (2006.01)
*A61K 31/085* (2006.01)
*A61P 35/04* (2006.01)
*C07C 43/275* (2006.01)

(52) U.S. Cl. ........................ 560/180; 560/194
(58) Field of Classification Search ........................ None
See application file for complete search history.

(56) References Cited

U.S. PATENT DOCUMENTS

| 5,135,746 | A  | * | 8/1992  | Matsuno et al. | ............... 424/725 |
| 2008/0194702 | A1 | * | 8/2008  | Kwon et al. | ............... 514/719 |
| 2008/0312337 | A1 | * | 12/2008 | Kwon et al. | ............... 514/701 |
| 2010/0125103 | A1 | * | 5/2010  | Huh et al. | ............... 514/548 |

FOREIGN PATENT DOCUMENTS

| KR | 10-0426450 | 4/2004 |
| KR | 10-0548743 | 2/2006 |
| KR | 10-0799266 | 1/2008 |
| WO | WO 2006/121258 A1 * | 11/2006 |

OTHER PUBLICATIONS

Ito et al., Obovatol and Obovatal, Novel Biphenyl Ether Lignans from the leaves of *Magnolia obovata* Thunb, Chem. Pharm. Bull., vol. 30, No. 9, May 1982, pp. 3347-3353.*
Denicourt, C., et al.,"Targeting Apoptotic Pathways in Cancer Cells", www.sciencemag.org, *Science*, vol. 305, pp. 1411-1413, (Sep. 3, 2004).
Reed, J. C., "Apoptosis-Based Therapies", *Natural Reviews/Drug Discovery*, vol. 1, pp. 111-121, (Feb. 2002).
Thomas Walle, "Methylation of Dietary Flavones Greatly Improves Their Hepatic Metabolic Stability and Intestinal Absorption", Molecular Pharmaceutics, vol. 4, No. 6, pp. 826-832.

* cited by examiner

*Primary Examiner* — Rosalynd Keys
(74) *Attorney, Agent, or Firm* — The Nath Law Group; Tanya E. Harkins; Mihsuhn Koh

(57) ABSTRACT

Disclosed herein are novel obovatol derivatives represented by Chemical Formula 1, and pharmaceutically acceptable salts thereof. Having the ability to inhibit the growth of cancer cells and induce apoptosis in cancer cells, the derivatives or pharmaceutically acceptable salts thereof are useful in the prevention and treatment of cancer and in the suppression of cancer metastasis. Also, a method for preparing the derivatives, and pharmaceutical compositions comprising the derivatives as active ingredients are disclosed.

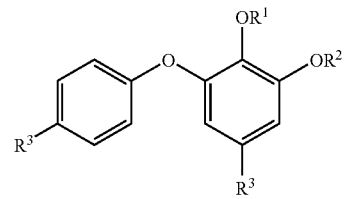

[Chemical Formula 1]

wherein $R^1$, $R^2$ and $R^3$ are as defined in the specification.

2 Claims, 1 Drawing Sheet

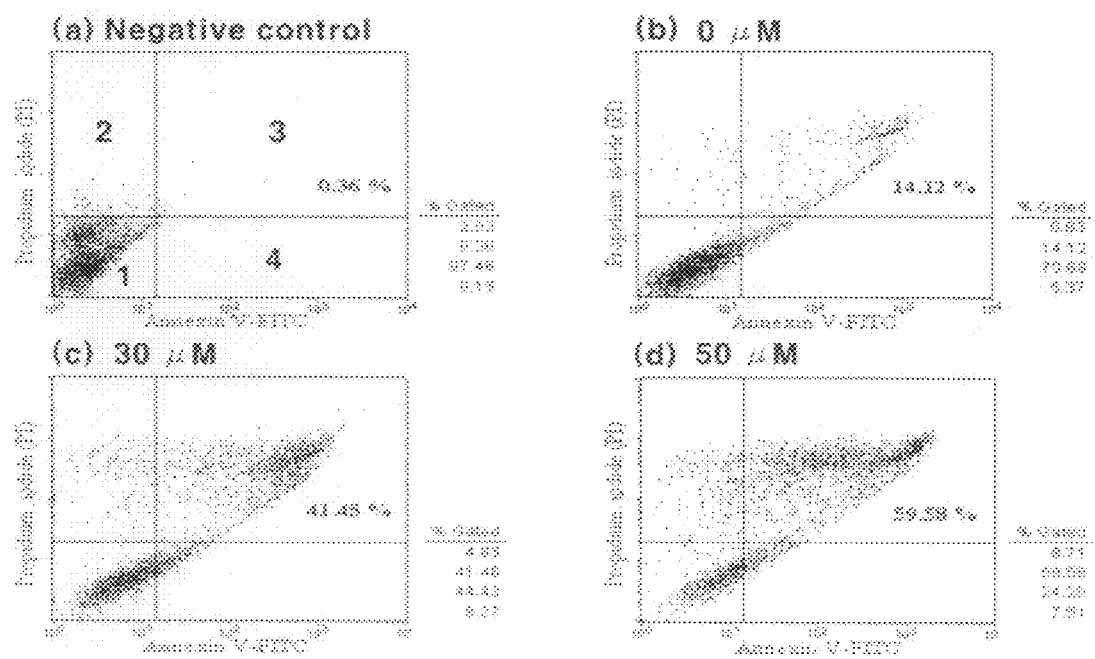

OBOVATOL DERIVATIVES OR PHARMACEUTICALLY ACCEPTABLE SALTS THEREOF, PREPARATION METHOD THEREOF AND PHARMACEUTICAL COMPOSITION FOR THE PREVENTION AND TREATMENT OF CANCER CONTAINING THE SAME AS AN ACTIVE INGREDIENT

BACKGROUND OF THE INVENTION

1. Field of the Invention

The present invention relates to a novel obovatol derivative or a pharmaceutically acceptable salt thereof, a method for preparing the same, and a pharmaceutical composition for the prevention and treatment of cancer comprising the same as an active ingredient.

2. Description of the Related Art

With the development of civilization, the incidence of cancer has increased. The treatment of cancer is, for the most part, dependent on surgical therapy, radiation therapy and chemical therapy, with 40 anticancer agents showing strong cytotoxicity. However, because the application of these therapies is limited to cancer patients in early stages, or to certain types of cancers, cancer morbidity remains on an increasing trend.

In order to differentiate malignant tumors from benign ones, they should show malignant properties including cell growth promotion and invasion into adjacent tissues, and something that overcomes growth control signals from adjacent tissues is another criterion. Signaling pathways in normal cells comprise only growth promoting signals, but also convey growth-controlling messages from the outer surface deep into the nucleus. In cancer cells, however, signaling chains between cell growth inhibitory factors are loosened or broken. In addition, cancer cells even neglect the signals induced from potential inhibitory factors present on the surface thereof. In many cancer cells, a series of important inhibitory factors induced by cancer suppressor genes are lost or inactivated (Bruce A. J. Ponder, Nature, 411, 336-341, 2001).

Taken together, recent study results demonstrate that it is the molecular apparatus, known as the cell cycle clock, present in the nucleus that is ultimately affected by cell growth factors and growth inhibitory factors. All cancer cells undergo cell division at very high rates without the ability to regulate the cell cycle. In normal cells, all of the signals transferred thereinto are collectively regulated to thus determine the phase of the cell cycle to which each cell progresses. If a decision is made to conduct cell division, the cell cycle starts to work (Gerard I. Evan and Karen H. Vousden. Nature, 411, 342-348, 2001).

Two mechanisms are described above for regulating the growth of normal cells to suppress cancer generation. That is, they are to suppress cell growth factors or activate cell growth inhibitory factors. Despite the normal operation of the two regulating mechanisms, cells may be activated by themselves, or may replicate continuously regardless of external cell division stop signals so as to finally progress into cancer. Further, excessive genetic mutations within cells may incite cells to become cancerous in spite of all body defense functions.

Each human cell has a self-destruction function which starts to work when its fundamental constituents are damaged or its regulation system is not controlled. This phenomenon is called apoptosis. For example, damage to nuclear genes may induce programmed cell death. Further, many research groups have recently reported that the functional loss of tumor suppressor genes within cells as well as the expression of oncogenes induce apoptosis. The destruction of damaged cells is disadvantageous to the cells themselves, but is very useful for the body in its entirety. The destruction of cells in which oncogenic modification occurs functions to remove the potential risk of cancer. On rare occasions, if they do not experience cell death, genetically modified cells become cancerous (Andy Catherine Denicourt and Steven F. Dowdy, Science, 305, 1411-1413, 2004).

Ongoing cancer cells have tactics for avoiding cell death. The tumor suppressor factor p53 has an anti-cancer mechanism for inducing cells to destroy themselves. The cells in which this protein is inactivated have weakened self-destruction functions. Additionally, cancer cells produce the Bcl-2 protein in a large amount to avoid cell death. Recent studies have disclosed that interfering with cell death not only causes the spread of tumors, but also induces the resistance of tumor cells to chemicals, resulting in danger to cancer patients. Over the years, it has been believed that radiotherapy and various chemical therapies directly kill malignant cells by destroying a wide range of their genes. Nonetheless, cancer cells have the ability to avoid cell death and become resistant to cancer drugs. These research results suggest that radiation and chemical therapies capable of inducing apoptosis, if developed, may be effective weapons against cancer (John C. Reed, Nature Review Drug Discovery 1, 111-121, 2002).

Apoptosis-inducing materials can be found in the prior art. For example, Korean Patent Publication No. 2006-0000241 discloses a twin compound, synthesized through the pharmaceutical association of an anticancer drug with DMNQ, which acts specifically on human cancer cell lines A549, HT-1080, SK-OV-3 and U937 and can induce apoptosis in two p53-mutated kinds of the human pulmonary epithelial cell line A549.

Korean Patent No. 426450 teaches an anti-cancer composition comprising as active ingredients citric acid, albumin and zinc in pharmaceutically effective amounts in combination with a pharmaceutically acceptable carrier or diluent.

Korean Patent No. 548743 describes a novel inhibitor F-3-2-5, isolated from a soil actinomycetes culture, capable of inducing apoptosis in cancer cells, a preparation method thereof, and its use in anti-cancer agents.

Korean Patent No. 799266 discloses a composition for the prevention and treatment of cancer comprising widdrol, isolated from a *Juniperus chinensis* extract, as an active ingredient.

As such, a lot of effort has been made in organic synthesis and natural material fields to develop apoptosis-inducing materials.

However, there is still a need for anticancer materials that are harmless to the human body and highly effectively exert growth regulation and apoptosis on cancer cells without side effects.

SUMMARY OF THE INVENTION

Leading to the present invention, intensive and thorough research into the development of compounds which are harmless to the body and have excellent inhibitory and apoptotic activity against cancer cells without side effects, conducted by the present inventors, resulted in the finding that obovatol derivatives, chemically modified from obovatol, which is obtainable from the herb-medicinally useful material *Magnolia obovata* Thunberg (Magnoliaceae), inhibit the growth of a variety of human cancer cell lines and induce apoptosis therein.

It is therefore an object of the present invention to provide a novel obovatol derivative or a pharmaceutically acceptable salt thereof.

It is another object of the present invention to provide a method for preparing the novel obovatol derivative or the pharmaceutically acceptable salt thereof.

It is a further object of the present invention to provide a pharmaceutical composition for the prevention and treatment of cancer comprising the novel obovatol derivative or the pharmaceutically acceptable salt as an active ingredient.

BRIEF DESCRIPTION OF THE DRAWINGS

FIG. 1 is FACS plots showing the apoptotic effect of the obovatol on colorectal cancer cells as V-FITC stained cell fractions ((a) negative control, (b) 0 μM of the obovatol derivative of Example 1, (c) 30 μM of the obovatol derivative of Example 1, (d) 50 μM of the obovatol derivative of Example 1).

DESCRIPTION OF THE PREFERRED EMBODIMENTS

The present invention pertains to obovatol derivatives represented by the following chemical formula 1 or pharmaceutically acceptable salts thereof.

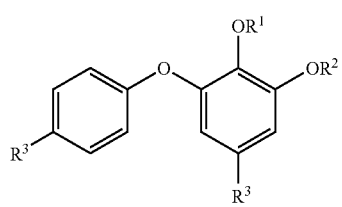

Chemical Formula 1 wherein, $R^1$ and $R^2$ are independently or optionally hydrogen, $C_1$-$C_4$ straight or branched alkyl, acetyl, $C_1$-$C_4$ alkoxy or $C_1$-$C_4$ alkoxyacetyl; and $R^3$ is hydrogen, $C_1$-$C_4$ straight or branched alkyl, $C_1$-$C_4$ alkenyl or allyl.

In Chemical Formula 1, preferably, $R^1$ and $R^2$ are independently or optionally methyl, ethyl, acetyl, methoxy, methoxyacetyl or ethoxyacetyl; and $R^3$ is hydrogen, propyl, propenyl or allyl.

Concrete examples of the obovatol derivatives represented by Chemical Formula 1 include:

1) 3-(4-propylphenoxy)-5-propylbenzene-1,2-diol;
2) 3-(4-allylphenoxy)-5-allyl-2-methoxyphenol;
3) 1-(4-allylphenoxy)-5-allyl-2,3-diacetyloxybenzene;
4) 1-(4-allylphenoxy)-5-allyl-2,3-di-2-methoxyacetyloxybenzene;
5) 3-(4-propylphenoxy)-2-methoxy-5-propylphenol;
6) 1-(4-propylphenoxy)-2,3-diacetyloxy-5-propylbenzene;
7) 1-(4-propylphenoxy)-2,3-di-2-methoxyacetyloxy-5-propylbenzene;
8) 3-(4-((E)-prop-1-enyl)phenoxy)-5-((E)-prop-1-enyl)benzene-1,2-diol;
9) 1-(4-((E)-prop-1-enyl)phenoxy)-2,3-diacetyloxy-5-((E)-prop-1-enyl)benzene; and
10) 1-(4-((E)-prop-1-enyl)phenoxy)-2,3-di-2-methoxyacetyloxy-5-((E)-prop-1-enyl)benzene.

The obovatol derivatives of the present invention, represented by Chemical Formula 1, may be used in the form of pharmaceutically acceptable salts. Useful are acid addition salts formed of pharmaceutically acceptable free acids. The term "pharmaceutically acceptable salt" as used herein refers to any organic or inorganic salt of the base compounds of Chemical Formula 1, not exhibiting a side effect in which the beneficial activity of the base compounds of Chemical Formula 1 is degraded when it is present at a concentration causing no toxicity and harm in the body. The free acids may be inorganic or organic. Examples of useful inorganic free acids include hydrochloric acid, bromic acid, nitric acid, sulfuric acid, perchloric acid and phosphoric acid. As organic acids, citric acid, lactic acid, maleic acid, fumaric acid, gluconic acid, methane sulfonic acid, acetic acid, gluconic acid, succinic acid, tartaric acid, 4-toluenesulfonic acid, galacturonic acid, embonic acid, glutamic acid, aspartic acid, oxalic acid, (D)-or (L)-malic acid, ethane sulfonic acid, p-toluene sulfonic acid, salicylic acid or malonic acid may be used. The pharmaceutically acceptable salts may include alkali metal salts (sodium salt, potassium salt, etc.) and alkaline earth metal salts (calcium salt, magnesium salt, etc.). Acid addition salts useful in the present invention include, but are not limited to, acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate, aluminum salt, arginine, benzathine, calcium, choline, diethylamine, diolamine, glycine, lysine, magnesium, meglumine, alamine, potassium salt, sodium salt, tromethamine, and zinc salt, with hydrochloride or trifluoroacetate being preferred.

Also, the obovatol derivatives of the present invention, represented by Chemical Formula 1, may be in the form of conventionally producible salts, hydrates, and solvates thereof as well as pharmaceutically acceptable salts.

Addition salts according to the present invention may be prepared using a conventional method. For example, they may be prepared by dissolving the compound of Chemical Formula 1 in a water-miscible organic solvent, such as acetone, methanol, ethanol or acetonitrile, and adding an excess of organic acids or an excess of aqueous inorganic acid solutions so as to precipitate or crystallize salts. These addition salts may be obtained by distilling the solvent or excess of acids from the solution or by suctioning and filtering the precipitates.

Also, the present invention is concerned with a method for the preparation of the obovatol derivatives represented by Chemical Formula 1.

In accordance with an embodiment of the present invention, the method for the preparation of the obovatol derivatives, as illustrated by the following Reaction Scheme 1, comprises the reaction of an obovatol (2) with hydrogen in the presence of a Pd-charcoal catalyst in a reaction solvent to afford an obovatol derivative (1a).

[Reaction Scheme 1]

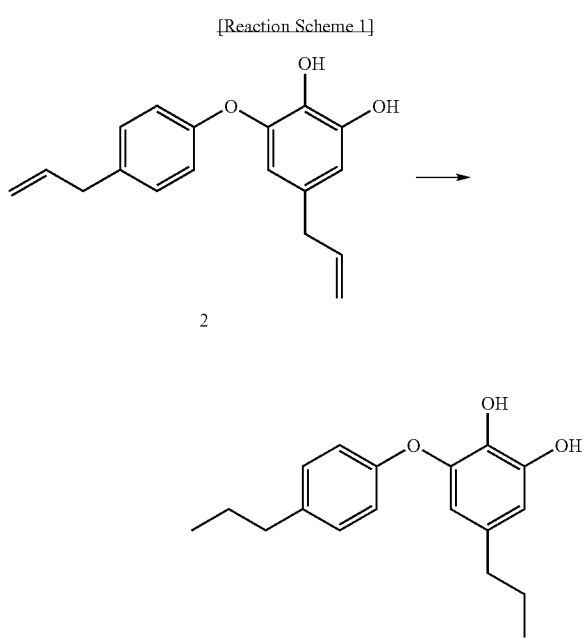

(wherein, compound 1a is a compound according to Chemical Formula 1).

The obovatol (2), serving as a starting material in Reaction Scheme 1, may be extracted from *Magnolia obovata* Thunberg (Magnoliaceae) according to the present invention or a method known in the art, may be chemically synthesized, or may be commercially available. Preferably, obovatol is extracted from *Magnolia obovata* Thunberg (Magnoliaceae) according to the present invention.

In greater detail, obovatol may be prepared by (a) soaking leaves of *Magnolia obovata* in an organic solvent to afford an extract; and (b) fractioning the extract in silica gel chromatography to isolate pure obovatol.

First, Step (a) is to dissolve obovatol present in leaves of *Magnolia obovata* in an organic solvent.

No limitations are imposed with respect to the leaves of *Magnolia obovata*. They may be cultured or commercially procured. The leaves are washed until clean and dried. Then, they are sectioned into desired sizes and added to a suitable volume of an organic solvent, preferably methanol. After the leaf sections are left for 24~50 hours at room temperature, the organic solvent is filtered through a filter. The filtrate may be then subjected to an additional process such as concentration or lyophilization.

Next, step (b) is to purify obovatol from the filtered organic solvent of step (a) using silica gel chromatography.

The organic layer thus formed is concentrated and the residue is purified by silica gel column chromatography using a mixture of chloroform and methanol, and is eluted with an elution solvent of various ratios (9:1-6:4) of chloroform and methanol.

The compound may be isolated by silica gel chromatography eluting with a mixture of ethyl acetate and hexane chloroform (90:10~80:20 v/v) as a mobile phase, with methylene chloride serving as a solvent. The resulting eluate may be further purified by $C_{18}$ column chromatography.

In the method according to an embodiment of the present invention, the reaction solvent where the reaction of an obovatol (2) with hydrogen in the presence of a Pd-charcoal catalyst occurs may be ethylacetate, acetone, or acetonitrile.

In the method of the present invention, obovatol is preferably reacted with hydrogen at a molar ratio of 1:10~1:50. This hydrogenation is preferably conducted at 20~25°C. for 10~12 hours. Reaction conditions beyond these limits may result in a decrease in production yield.

In accordance with another embodiment of the present invention, the method for the preparation of the obovatol derivatives, as illustrated by the following Reaction Scheme 2, comprises the tautomerization of an obovatol (2) into an obovatol derivative (1b) in the presence of a palladium chloride ($PdCl_2$) catalyst in an alcohol solvent.

[Reaction Scheme 2]

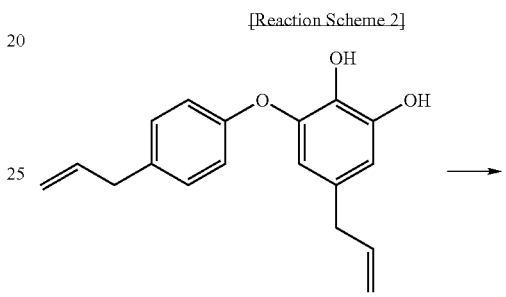

(wherein, compound 1b is a compound according to Chemical Formula 1)

In the preparation method of obovatol derivatives according to the present invention, the alcohol solvent may be methanol or ethanol.

In this preparation method, the obovatol (2) is preferably reacted with palladium chloride at a molar ratio of 1:0.01~1:0.02. Also, the tautomerization is preferably carried out at 20~25°C. for 2~3 hours. Reaction conditions beyond these limits may result in a decrease in production yield.

In accordance with a further embodiment of the present invention, the method for the preparation of the obovatol derivatives, as illustrated by the following Reaction Scheme 3, comprises the reaction of a compound of Chemical Formula 3 (compound 1a or 1b prepared in Reaction Scheme 1 or 2, or obovatol) with a compound of Chemical Formula 4 in the presence of potassium carbonate ($K_2CO_3$) in a solvent to afford the obovatol derivative 1.

[Reaction Scheme 3]

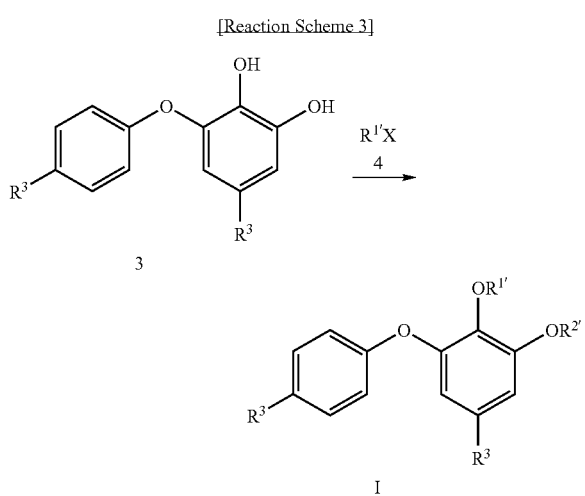

(wherein, $R^3$ is as defined in Reaction Scheme 1, $R^{1'}$ is the same as $R^1$ except for hydrogen, $R^{2'}$ is hydrogen or $R^{1'}$, and X is a halogen element)

In the method of preparing obovatol derivatives according to Reaction Scheme 3, the reaction solvent may be methyl acetate, acetone, or acetonitrile.

In this method, the compound of Chemical Formula 3 is preferably reacted with the compound of Chemical Formula 4 at a molar ratio of 1:1.1~1:1.2. This reaction is preferably carried out at 20~25°C. for 5~6 hours. Reaction conditions beyond these limits may result in a decrease in production yield.

The compounds thus prepared can be isolated using silica gel column chromatography. They were identified as obovatol derivatives using UV and IR spectra, high resolution mass spectrometry and NMR.

In addition, the present invention provides to a pharmaceutical composition for the prevention and treatment of cancer comprising an obovatol derivative represented by Chemical Formula 1 or a pharmaceutically acceptable salt thereof as an active ingredient.

Further, the present invention provides to a method for treating cancer, comprising administering the obovatol derivative of Chemical Formula 1 or a pharmaceutically acceptable salt thereof at a therapeutically effective dose to a patent in need thereof.

The obovatol derivatives of Chemical Formula 1 according to the present invention were found to effectively inhibit the growth of cancerous tissues as assayed in in vivo experiments in which the obovatol derivatives were administered to immune-deficient mice implanted with a colorectal cancer cell line (see Table 3). Also, the obovatol derivatives of Chemical Formula 1 according to the present invention were proven to effectively induce cancer cells to undergo apoptosis (FIG. 1). Therefore, the obovatol derivatives or pharmaceutically acceptable salts thereof in accordance with the present invention are useful in the prevention and treatment of cancer.

Examples of the cancer to which the obovatol derivatives or pharmaceutically acceptable salts are therapeutically applicable include, but are not limited to, large intestine cancer, stomach cancer, prostate cancer, breast cancer, renal cancer, liver cancer, brain tumors, lung cancer, uterine cancer, colorectal cancer, bladder cancer, pancreatic cancer, and blood cancer.

The term "anti-cancer" as used herein is intended to refer to the inhibition or interruption of the formation or proliferation of cancer cells, thus leading to the prevention and treatment of cancer.

The term "prevention" as used herein with respect to cancer, means any action inhibiting the formation of cancer or delaying the outbreak of cancer, including the administration of a pharmaceutical composition. By the term "treatment" as used herein with respect to diseases is meant any action by which the symptoms of the diseases take a turn for the better or are alleviated.

As used herein, the term "administration" means the provision of a therapeutically effective material for patients using any suitable method. As long as it allows the composition of the present invention to arrive at a target tissue, any administration route may be taken in the present invention. In this regard, the composition of the present invention may be administered orally or parenterally. The administration of the composition according to the present invention may be aided by a device which facilitates the delivery of the active ingredient to target cells.

The pharmaceutical composition according to the present invention is usually formulated in combination with a diluent or excipient, such as a filler, a thickening agent, a binder, a wetting agent, a disintegrant, a surfactant, etc.

Solid preparations intended for oral administration of the compound of the present invention may take the form of tablets, pills, powders, granules, capsules, troches, and the like. These solid preparations are formulated in combination with at least one excipient such as starch, calcium carbonate, sucrose, lactose, or gelatine. In addition, a lubricant such as magnesium stearate, talc, or the like may also be added. Liquid preparations intended for oral administration include suspensions, internal use solutions, emulsion, syrups, and the like. In addition to a simple diluent such as water or liquid paraffin, various excipients, such as wetting agents, sweetening agents, aromatics, preservatives, and the like may be contained in the liquid preparations for the oral administration of the compound of the present invention.

Also, the compound of the present invention may be administered via a non-oral route. For this, sterile aqueous solutions, non-aqueous solvents, suspensions, emulsions, lyophilizates, suppositories, and the like may be used. Injectable propylene glycol, polyethylene glycol, vegetable oils such as olive oil, and esters such as ethyl oleate may be suitable for non-aqueous solvents and suspensions. The basic materials of suppositories include Witepsol, macrogol, Tween 61, cacao butter, laurin butter, glycerol, and gelatin.

The composition of the present invention is administered in a therapeutically effective amount. The term "therapeutically effective amount" as used herein means an amount of the composition that is sufficient to affect the anticancer activity of the obovatol at a reasonable benefit/risk ratio applicable to any medical treatment. The specific therapeutically effective dose level for any particular patient will depend upon a variety of factors including the disorder being treated and the severity of the disorder, the activity of the compound employed, body sensitivity to the compound, the time of administration, route of administration, rate of excretion, the duration of the treatment, drugs used in combination or coincidental therapy, and other factors known in the art. The composition of the present invention may be administered alone or in combination with other agents. In the latter case, they may be administered sequentially or simultaneously. It is important to administer the compound at the minimal dose at which the maximal medicinal effect is obtained without side effects, which can be readily determined by those skilled in the art.

For example, the effective dose of the compound according to the present invention may vary depending on age, sex and body weight. Typically, the compound according to the present invention may be administered at a dose from 1 to 50 mg per kg of body weight, and preferably at a dose from 1 to 10 mg per kg of body weight every day or every other day. The compound may be administered in a single dose or may be divided into three doses per day according to the instructions of a physician or pharmacist. However, the dose does not limit the present invention in any way because it may vary with administration route, disease severity, sex, weight, age, etc.

A better understanding of the present invention may be obtained through the following examples which are set forth to illustrate, but are not to be construed as the limit of the present invention.

EXAMPLE 1

Synthesis of 3-(4-Propylphenoxy)-5-Propylbenzene-1,2-Diol

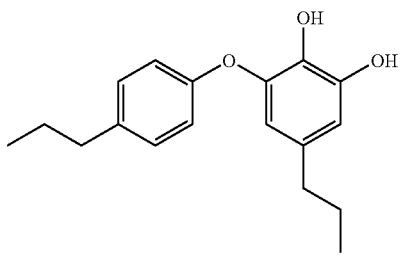

After being isolated from the leaves of *Magnolia obovata* (growing naturally in the central region of Korea), obovatol (1 g) was dissolved in acetone (200 ml) and added to Pd-charcoal (2 mg) at room temperature. Hydrogen was allowed to flow into the catalyst.

Subsequently, the organic layer containing an active material was collected and concentrated in a vacuum. The concentrate (1.1 g) was dissolved in methylene chloride (100 ml) and loaded onto a silica gel (Merck, Art No. 9385) so as to adsorb the active material thereonto. Silica gel column chromatography eluting with a gradient of a mixture of ethylacetate and hexane from 10:90 to 20:80 afforded colorless 3-(4-propylphenoxy)-5-propylbenzene-1,2-diol (0.9 g, yield 90%).

EXAMPLE 2

Synthesis of 3-(4-Allylphenoxy)-5-Allyl-2-Methoxyphenol

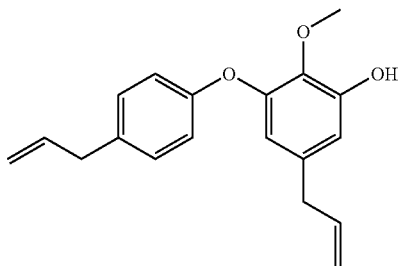

To a solution of obovatol (1 g) in acetone (200 ml) were added potassium carbonate ($K_2CO_3$) (1.1 g) and methyl iodide (0.3 g), followed by stirring the solution at room temperature for 5 hours. After completion of the reaction, the organic layer containing the active material was collected and concentrated in a vacuum. The concentrate (1.2 g) was dissolved in methylene chloride (30 ml) and loaded onto a silica gel (Merck, Art No. 9385) so as to adsorb the active material thereonto. Silica gel column chromatography eluting with a gradient of a mixture of ethylacetate and hexane from 10:90 to 20:80 afforded colorless 3-(4-allylphenoxy)-5-allyl-2-methoxyphenol (0.91 g, yield 90%).

EXAMPLE 3

Synthesis of 1-(4-Allylphenoxy)-5-Allyl-2,3-Diacetyloxybenzene

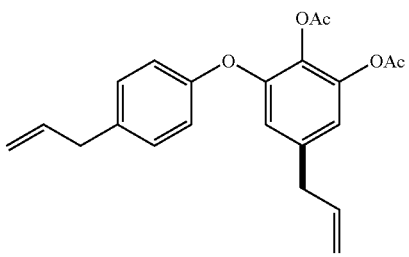

The same procedure as in Example 2 was performed, with the exception that potassium carbonate ($K_2CO_3$) (1.2 g) and acetyl chloride (500 mg) were added to a solution of obovatol (1 g) in acetone (200 ml) and stirred at room temperature for 5 hours, to afford colorless 1-(4-allylphenoxy)-5-allyl-2,3-diacetyloxybenzene (1.2 g, yield 90%)

EXAMPLE 4

Synthesis of 1-(4-Allylphenoxy)-5-Allyl-2,3-di-2-Methoxyacetyloxybenzene

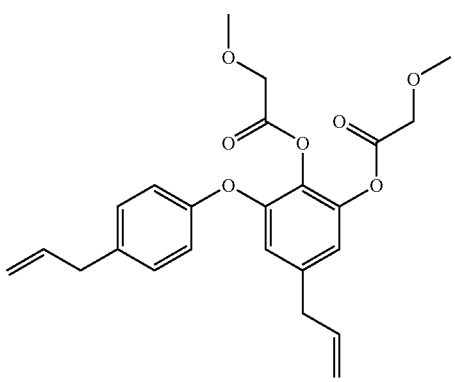

The same procedure as in Example 2 was performed, with the except that potassium carbonate ($K_2CO_3$) (1.2 g) and acetyl chloride (1 mg) were added to a solution of obovatol (1 g) in acetone (200 ml) and stirred at room temperature for 5 hours, to afford colorless 1-(4-allylphenoxy)-5-allyl-2,3-di-2-methoxyacetyloxybenzene (1.3 g, yield 90%)

EXAMPLE 5

Synthesis of 3-(4-Propylphenoxy)-2-Methoxy-5-Propylphenol

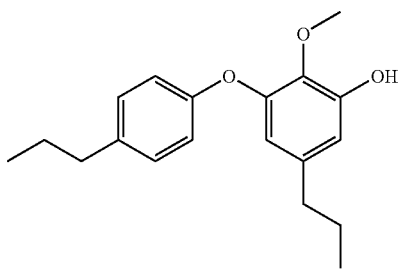

The same procedure as in Example 2 was performed, with the exception that potassium carbonate (K$_2$CO$_3$) (1.1 g) and methyl iodide (0.3 g) were added to a solution of tetrahydroobovatol (1 g), prepared in Example 1, in acetone (200 ml) and stirred at room temperature for 5 hours, to afford colorless 3-(4-propylphenoxy)-2-methoxy-5-propylphenol (1 g, yield 90%)

EXAMPLE 6

Synthesis of 1-(4-Propylphenoxy)-2,3-Diacetyloxy-5-Propylbenzene

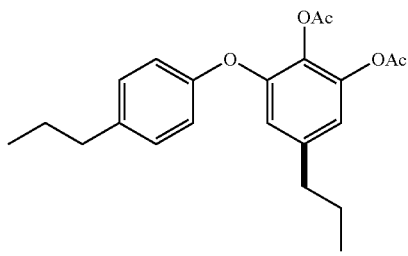

The same procedure as in Example 2 was performed, with the exception that potassium carbonate (K$_2$CO$_3$) (1.1 g) and acetyl chloride (500 mg) were added to a solution of tetrahydroobovatol (1 g), prepared in Example 1, in acetone (200 ml) and stirred at room temperature for 5 hours, to afford colorless 1-(4-propylphenoxy)-2,3-diacetyloxy-5-propylbenzene (1.1 g, yield 90%)

EXAMPLE 7

Synthesis of 1-(4-Propylphenoxy)-2,3-di-2-Methoxyacetyloxy-5-Propylbenzene

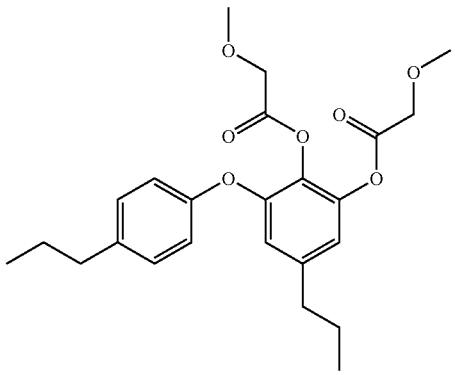

The same procedure as in Example 2 was performed, with the exception that potassium carbonate (K$_2$CO$_3$) (1.1 g) and methoxyacetyl chloride (500 mg) were added to a solution of tetrahydroobovatol (1 g), prepared in Example 1, in acetone (200 ml) and stirred at room temperature for 5 hours, to afford colorless 1-(4-propylphenoxy)-2,3-di-2-methoxyacetyloxy-5-propylbenzene (1.2 g, yield 90%)

EXAMPLE 8

Synthesis of 3-(4-((E)-Prop-1-enyl)Phenoxy)-5-((E)-Prop-1-enyl) Benzene-1,2-Diol

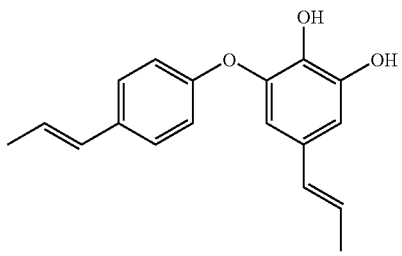

To a solution of obovatol (1 g) in methanol was added palladium chloride (PdCl$_2$) (10 mg), followed by stirring at room temperature for 5 hours. After completion of the reaction, the organic layer containing the active material was collected and concentrated in a vacuum. The concentrate (1.1 g) was dissolved in methylene chloride (30 ml) and loaded onto a silica gel (Merck, Art No. 9385) so as to adsorb the active material thereonto. Purification through silica gel column chromatography eluting with a gradient of a mixture of ethylacetate and hexane from 10:90 to 20:80 afforded colorless 3-(4-((E)-prop-1-enyl)phenoxy)-5-((E)-prop-1-enyl) benzene-1,2-diol (0.91 g, yield 90%)

EXAMPLE 9

Synthesis of 1-(4-((E)-Prop-1-enyl)Phenoxy)-2,3-Diacetyloxy-5-((E)-Prop-1-enyl) Benzene

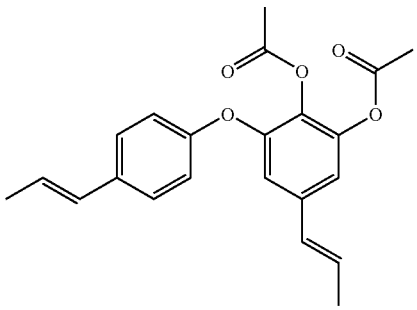

The same procedure as in Example 2 was performed, with the exception that potassium carbonate ($K_2CO_3$) (1.3 g) and acetyl chloride (500 mg) were added to a solution of propenylobovatol (1 g), prepared in Example 8, in acetone (200 ml) and stirred at room temperature for 5 hours, to afford colorless 1-(4-((E)-prop-1-enyl)phenoxy)-2,3-diacetyloxy-5-((E)-prop-1-enyl) benzene (1.0 g, yield 90%)

EXAMPLE 10

Synthesis of 1-(4-((E)-Prop-1-enyl)Phenoxy)-2,3-di-2-Methoxyacetyloxy-5-((E)-Prop-1-enyl)Benzene

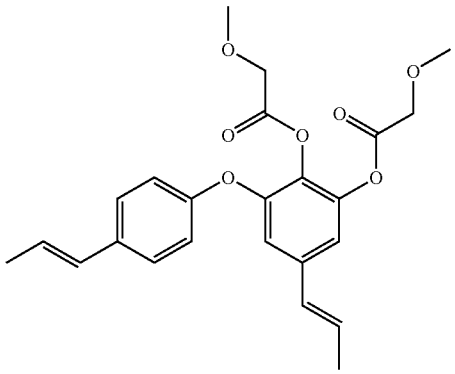

The same procedure as in Example 2 was performed, with the exception that potassium carbonate ($K_2CO_3$) (1.2 g) and methoxyacetyl chloride (600 mg) were added to a solution of propenylobovatol (1 g), prepared in Example 8, in acetone (200 ml) and stirred at room temperature for 5 hours, to afford colorless 1-(4-((E)-prop-1-enyl)phenoxy)-2,3-di-2-methoxyacetyloxy-5-((E)-prop-1-enyl)benzene (1.15 g, yield 90%)

<Analysis>

The compounds prepared in Examples 1~10 were analyzed for molecular weight and molecular formula by UV spectrometry, IR (infrared) spectrometry and high resolution mass spectrometry. In detail, the analysis was conducted using a Shimadzu UV-265 spectrophotometer for UV absorbance, a Bio-Rad Digilab Division FTS-80 spectrophotometer for IR absorbance, and a VG70-SEQ mass spectrometer (MS) for molecular weight and molecular formula. Also, $^1H$ and $^{13}C$-NMR spectra were obtained using an NMR system (Varian 300 MHz, 500 MHz NMR). From the spectra, the structures of the compounds were determined.

Analysis results are summarized in Tables 1 and 2, below.

TABLE 1

Appearance, Molecular Formula, Molecular Weight and Solubility

| Cpd. | Color | Molecular Formula | Mw | Solubility Soluble | Insoluble |
|---|---|---|---|---|---|
| Ex. 1 | Colorless | $C_{18}H_{22}O_3$ | 282 | Alcohol, DMSO | Water |
| Ex. 2 | Colorless | $C_{19}H_{20}O_3$ | 296 | Alcohol, DMSO | Hexane, Water |
| Ex. 3 | Colorless | $C_{22}H_{22}O_5$ | 366 | Alcohol, DMSO | Hexane, Water |
| Ex. 4 | Colorless | $C_{24}H_{26}O_7$ | 426 | Alcohol, DMSO | Hexane, Water |
| Ex. 5 | Colorless | $C_{19}H_{24}O_3$ | 300 | Alcohol, DMSO | Hexane, Water |
| Ex. 6 | Colorless | $C_{22}H_{26}O_3$ | 370 | Alcohol, DMSO | Water |
| Ex. 7 | Colorless | $C_{24}H_{30}O_7$ | 430 | Alcohol, DMSO | Water |
| Ex. 8 | Colorless | $C_{18}H_{18}O_3$ | 282 | Alcohol, DMSO | Water |
| Ex. 9 | Colorless | $C_{22}H_{22}O_5$ | 366 | Alcohol, DMSO | Water |
| Ex. 10 | Colorless | $C_{24}H_{26}O_7$ | 426 | Alcohol, DMSO | Water |

TABLE 2

NMR Data

| Cpd. | NMR Data |
|---|---|
| Ex. 1 | $^1$H-NMR (CDCl$_3$): 7.13 (H-3' and H-5', d, J = 8.7 Hz), 6.95 (H-2' and H-6', d, J = 8.7 Hz), 6.57 (H-6, d, J = 1.5 Hz), 6.3 (H-4, d, J = 2.1 Hz), 2.58 (H-7, t, J = 8.1 Hz), 2.42 (H-7', t, J = 8.1 Hz), 1.59 (H-8 and H-8', m), 0.92 (H-9 and H-9', m). |
| Ex. 2 | $^1$H-NMR (CDCl$_3$): 7.12 (H-3' and 5', d, J = 8.7 Hz), 6.92 (H-2' and H-6', d, J = 8.1 Hz), 6.56 (H-6, d, J = 2.1 Hz), 6.28 (H-4, d, J = 2.4 Hz), 5.97 (H-8 and H-8', m), 5.09 (H-9 and H-9', m), 3.89 (3H, s), 3.36 (H-7', d, J = 6.6 Hz), 3.23 (H-7, d, J = 6.6 Hz). |
| Ex. 3 | $^1$H-NMR (CDCl$_3$): 7.14 (H-3' and 5', d, J = 8.1 Hz), 6.93 (H-2' and H-6', d, J = 8.1 Hz), 6.76 (H-6, d, J = 2.1 Hz), 6.65 (H-4, d, J = 2.1 Hz), 5.92 (H-8 and H-8', m), 5.09 (H-9 and H-9', m), 3.36 (H-7', d, J = 6.6 Hz), 3.28 (H-7, d, J = 6.6 Hz), 2.28 (3H, s), 2.18 (3H, s). |
| Ex. 4 | $^1$H-NMR (CDCl$_3$): 7.13 (H-3' and 5', d, J = 8.7 Hz), 6.93 (H-2' and H-6', d, J = 8.7 Hz), 6.81 (H-6, d, J = 2.1 Hz), 6.67 (H-4, d, J = 2.1 Hz), 5.91 (H-8 and H-8', m), 5.09 (H-9 and H-9', m), 4.26 (3H, s), 4.14 (3H, s), 3.35 (2H, d, J = 6.6 Hz), 3.31 (2H, d, J = 6.6 Hz). |
| Ex. 5 | $^1$H-NMR (CDCl$_3$): 7.15 (H-3' and H-5', d, J = 9 Hz), 6.97 (H-2' and H-6', d, J = 9 Hz), 6.66 (H-6, d, J = 1.5 Hz), 6.37 (H-4, d, J = 1.5 Hz), 3.92 (3H, s), 2.61 (H-7, t, J = 8.1 Hz), 2.48 (H-7', t, J = 8.1 Hz), 1.65 (H-8 and H-8', m), 0.97 (H-9 and H-9', m). |
| Ex. 6 | $^1$H-NMR (CDCl$_3$): 7.12 (H-3' and H-5', d, J = 8.7 Hz), 6.92 (H-2' and H-6', d, J = 8.7 Hz), 6.74 (H-6, d, J = 2.1 Hz), 6.63 (H-4, d, J = 2.1 Hz), 2.56 (H-7, t, J = 8.1 Hz), 2.48 (H-7', t, J = 8.1 Hz), 2.29 (3H, s), 2.19 (3H, s), 1.59 (H-8 and H-8', m), 0.92 (H-9 and H-9', m). |
| Ex. 7 | $^1$H-NMR (CDCl$_3$): 7.12 (H-3' and H-5', d, J = 8 Hz), 6.93 (H-2' and H-6', d, J = 8 Hz), 6.79 (H-6, d, J = 2 Hz), 6.65 (H-4, d, J = 2 Hz), 4.25 (2H, s), 4.14 (2H, s), 3.52 (3H, s), 3.41 (3H, s), 2.56 (H-7, t, J = 7.5 Hz), 2.5 (H-7', t, J = 7.5 Hz), 1.59 (H-8 and H-8', m), 0.92 (H-9 and H-9', m). |
| Ex. 8 | $^1$H-NMR (CDCl$_3$): 7.28 (H-3' and 5', d, J = 9 Hz), 6.95 (H-2' and H-6', d, J = 9 Hz), 6.73 (H-6, d, J = 1.5 Hz), 6.42 (H-4, d, J = 1.5 Hz), 6.37 (H-7, d, J = 15.5 Hz), 6.15 (H-7' and H-8, m), 5.99 (H-8', m), 5.42 (2H, s), 1.88 (H-9, d, J = 7 Hz), 1.80 (H-9', d, J = 7 Hz). |
| Ex. 9 | $^1$H-NMR (CDCl$_3$): 7.27 (H-3' and 5', d, J = 8.1 Hz), 6.97 (H-2' and H-6', d, J = 8.1 Hz), 6.88 (H-6, d, J = 1.5 Hz), 6.75 (H-4, d, J = 1.5 Hz), 6.37 (H-7, d, J = 14.7 Hz), 6.14 (H-7', H-8 and H-8', m), 2.29 (3H, s), 2.18 (3H, s), 1.87 (H-9, d, J = 6.6 Hz), 1.81 (3H, d, J = 6.6 Hz). |

TABLE 2-continued

NMR Data

| Cpd. | NMR Data |
|---|---|
| Ex. 10 | $^1$H-NMR (CDCl$_3$): 7.27 (H-3' and 5', d, J = 8.1 Hz), 6.95 (H-2' and H-6', d, J = 8.1 Hz), 6.77 (H-6, d, J = 1.5 Hz), 6.17 (5H, m), 4.27 (2H, s), 4.14 (2H, s), 3.525 (3H, s), 3.41 (3H, s), 1.88 (H-9, d, J = 6.6), 1.83 (H-9', d, J = 6.6). |

EXPERIMENTAL EXAMPLE 1

Inhibitory Effect on Growth of Cancer Cell

The compounds prepared in Examples 1, 2 and 3 were evaluated for inhibitory activity against the growth of a human cancer cell line using WST-1. Human cancer cell lines were incubated in 10% fetal bovine serum (FBS)-supplemented media at 37°C. in a 5% CO$_2$ atmosphere, followed by detaching the cells with 0.05% trypsin-EDTA.

Cells were plated onto 90-well plates at a density of 4,000 cells (A549, MDA-MB-231), 5,000 cells (HEK293, NCI-H23) or 6,000 cells (HCA-7, HCT116, SW620, DU145) per well, which were counted using a hematocytometer.

After incubation in 10% FBS-supplemented media at 37°C. for 24 hours in a 5% CO$_2$ incubator, the media was changed with fresh media containing a control (0.1% DMSO) or the compound of Example 1 in an amount of 5, 10, 15, 20, 25 or 30 µg/ml (dissolved in DMSO and diluted in the medium). After 48 hours of treatment, WST-1 (Roche) was added in an amount of 10 µl to each well and incubated for 2 hrs. Absorbance at 450 nm was read in an ELISA reader (Bio-Rad).

The results are given in Table 3, below.

TABLE 3

| Compounds | OD |
|---|---|
| Control | 0.604 |
| Example 1 (5 µg/ml) | 0.592 |
| Example 1 (10 µg/ml) | 0.557 |
| Example 1 (15 µg/ml) | 0.474 |
| Example 1 (20 µg/ml) | 0.247 |
| Example 1 (25 µg/ml) | 0.149 |
| Example 1 (30 µg/ml) | 0.141 |

As seen in Table 3, the compound of Example 1, when present at a concentration of 20 µg/ml or higher, was observed to inhibit the growth of cancer cells by 50% or more.

EXPERIMENTAL EXAMPLE 2

Apoptotic Effect on Cancer Cells

The obovatol derivatives according to the present invention were assayed for ability to induce programmed cell death as follows.

Apoptosis was analyzed using flow cytometry. First, colorectal cancer cells (SW620) were treated with 0.1% DMSO (negative control), 0 µM, 30 µM or 50 µM of the compound of Example 1 for 48 hours and detached with 0.05% trypsin-EDTA. After being harvested through centrifugation, the cells were washed twice with PBS (phosphate-buffered saline) and suspended at a density of 1×10$^6$ cells/ml in a 1× binding buffer (10 mM Hepes/NaOH, pH 7.4, 140 mM NaCl, and 2.5 mM CaCl$_2$). 100 µl of the cell suspension was transferred into a 5 ml culture tube, mixed with 5 µl of annexin V-FITC and 10 µl of PI (propidium iodide), and incubated at room temperature for 15 min in a light-tight condition. Then, 400 µl of 1×binding buffer was added to each tube, followed by FACS analysis for annexin V-FITC-stained cells (Moussa Alkhalaf, Abdulla El-Mowafy, Waleed Renno, Ousama Rachid, Ahmed Ali, and Raja Al-Attyiah, Archives of Medical Research 39, 162-168, 2006).

The results are shown in FIG. 1.

In FACS plots of FIG. 1, the distribution of stained cells is shown. Cell migration to the second quadrant and the fourth quadrant refers to an increase in chromosome number, meaning an increased number of cells in the G2/M phase or S phase.

The third quadrant and the fourth quadrant of the FACS plot indicate cells expressing the early apoptosis marker annexin V.

As seen in FIG. 1, the fraction of the cells migrating to the third quadrant increased from 14.12% at pre-treatment to 59.58% after treatment with 50 µM of the obovatol derivative of the present invention, indicating that the obovatol derivatives of the present invention can increase the expression level of the early apoptosis marker annexin V, resulting in apoptosis induction.

Having the ability to induce apoptosis, therefore, the obovatol derivatives according to the present invention can be applied to the prevention and treatment of cancer.

EXPERIMENTAL EXAMPLE 3

Assay for Acute Oral Toxicity in Rat

The obovatol derivatives of the present invention were assayed in vivo for acute oral toxicity as follows.

Specific pathogen free (SPF) SD rats 6 weeks old were used for this assay. The obovatol derivative prepared in Example 1 or 2 was dissolved in distilled water, and the solution was orally administered at a dose of 500 mg/kg to respective groups of two rats.

After the oral administration, the rats were observed for death, clinical symptoms, changes in body weight, and the like, and subjected to hematological and serobiochemical tests. Autopsies were performed to check for abnormalities of the thoracic and abdominal organs with the naked eye. Neither particular clinical symptoms nor perished animals were observed. In addition, no acute toxicity was observed in body weight change, haematological tests, serobiochemical tests, or autopsy examination.

These results demonstrate the compounds tested do not induce toxicity up to a dose of 500 mg/kg in rats, and are proven safe with an LD$_{50}$ of 500 mg/kg or more upon oral administration.

FORMULATION EXAMPLE 1

Preparation of Pharmaceutical Preparation

| <1-1> Preparation of Powder | |
|---|---|
| Obovatol derivative of Chemical Formula 1 | 2 g |
| Lactose | 1 g |

The above ingredients were mixed and loaded into an airtight sac to produce a powder agent.

| <1-2> Preparation of Tablet | |
|---|---|
| Obovatol derivative of Chemical Formula 1 | 100 mg |
| Corn Starch | 100 mg |
| Lactose | 100 mg |
| Mg Stearate | 2 mg |

These ingredients were mixed and prepared into tablets using a typical tabletting method.

| <1-3> Preparation of Capsule | |
|---|---|
| Obovatol derivative of Chemical Formula 1 | 100 mg |
| Corn Starch | 100 mg |
| Lactose | 100 mg |
| Mg Stearate | 2 mg |

These ingredients were mixed and loaded into gelatin capsules according to a typical method to produce capsules.

| <1-4> Preparation of Injection | |
|---|---|
| Obovatol derivative of Chemical Formula 1 | 10 μg/ml |
| Dil. HCl BP | added to form pH 3.5 |
| NaCl BP injection | up to 1 ml |

The compound of the present invention was dissolved, along with mannitol and $Na_2HPO_4 \cdot 12H_2O$, in distilled water, and the pH of the solution was adjusted to 7.4 before sterilizing. An injection was prepared according to a typical procedure.

The obovatol derivative was dissolved in a suitable volume of an NaCl BP injection, and the solution was adjusted to a pH of 3.5 with diluted HCl BP and to a desired volume with an NaCl BP injection, followed by sufficient mixing. The solution was loaded into transparent 5 ml type I ampules, which were hermetically sealed by melting, followed by autoclaving at 120° C. for 15 min to prepare injections.

Having the excellent ability to inhibit the growth of cancer cells and induce apoptosis in cancer cells, the obovatol derivatives or pharmaceutically acceptable salts thereof in accordance with the present invention, as described above, are useful in the prevention and treatment of cancer and in the suppression of cancer metastasis.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A compound represented by the following Chemical Formula 1, or a pharmaceutically acceptable salt thereof

[Chemical Formula 1]

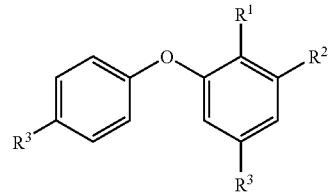

wherein, $R^1$ and $R^2$ are independently or optionally methoxyacetyl or ethoxyacetyl; and $R^3$ is propyl, or propenyl or allyl.

2. The compound of Chemical Formula 1 or the pharmaceutically acceptable salt as set forth in claim 1, wherein the compound is selected from the a group consisting of:

1-(4-allylphenoxy)-5-allyl-2,3-di-2-methoxyacetyloxybenzene;

1-(4-propylphenoxy)-2,3-di-2-methoxyacetyloxy-5-propylbenzene; and 1-(4-((E)-prop-1-enyl)phenoxy)-2,3-di-2-methoxyacetyloxy-5-((E)-prop-1-enyl)benzene.

* * * * *